US010971031B2

(12) United States Patent
Ortiz

(10) Patent No.: US 10,971,031 B2
(45) **Date of Patent: *Apr. 6, 2021**

(54) APPARATUS AND METHOD FOR IDENTIFYING FOOD NUTRITIONAL VALUES

(71) Applicant: Fitly Inc., Philadelphia, PA (US)

(72) Inventor: Caonabo Anthony Ortiz, Philadelphia, PA (US)

(73) Assignee: Fitly Inc., Philadelphia, PA (US)

( * ) Notice: Subject to any disclaimer, the term of this patent is extended or adjusted under 35 U.S.C. 154(b) by 1197 days.

This patent is subject to a terminal disclaimer.

(21) Appl. No.: 15/155,878

(22) Filed: May 16, 2016

(65) Prior Publication Data

US 2016/0260352 A1 Sep. 8, 2016

Related U.S. Application Data

(63) Continuation-in-part of application No. 14/848,992, filed on Sep. 9, 2015, now Pat. No. 9,349,297, and a (Continued)

(51) Int. Cl.

*A63F 9/24* (2006.01)
*G09B 19/00* (2006.01)

(Continued)

(52) U.S. Cl.

CPC .......... *G09B 19/0092* (2013.01); *A45C 11/00* (2013.01); *A45C 11/20* (2013.01); *A45C 15/00* (2013.01); *A47G 19/025* (2013.01); *A47G 19/027* (2013.01); *B65D 25/04* (2013.01); *B65D 43/02* (2013.01); *B65D 81/18* (2013.01); *G01G 17/00* (2013.01); *G01G 19/00* (2013.01); *G01G 19/414* (2013.01); *G01G 19/4146* (2013.01); *G01G 19/56* (2013.01); *G01G 23/36* (2013.01); *G01N 33/02* (2013.01);

(Continued)

(58) Field of Classification Search

CPC ... A47G 19/025; G06F 19/3475; A45C 11/20; A45C 15/00; B65D 25/04; G09B 19/0092

See application file for complete search history.

(56) References Cited

U.S. PATENT DOCUMENTS 2,889,443 A 6/1959 Dobmeier
6,457,250 B1 10/2002 Mingus et al.

(Continued)

FOREIGN PATENT DOCUMENTS

WO 2012115297 8/2012
WO 2014132559 9/2014
WO 2015000890 1/2015

*Primary Examiner* — Steve Rowland
(74) *Attorney, Agent, or Firm* — Eugene H. Nahm

(57) ABSTRACT

System and method for identifying, measuring and analyzing food nutritional values and consumer eating behaviors is disclosed. A food container, having weight sensors and food identification sensors, identifies weight, type, and preparation status of the food item being consumed by the user from the food container. Based on the identified information, the nutritional value of the food item is determined and observed. The food container in communication with the system components may provide the user a recommended meal plan to improve the user's health condition. In addition, the food container issues an alert to the user when the user puts too much, too less, or the right amount of food items in the food container or eats the food items too fast.

32 Claims, 10 Drawing Sheets

502 104 504 402 404 500 106 102 406 120 506

Related U.S. Application Data continuation-in-part of application No. 14/636,089, filed on Mar. 2, 2015, now Pat. No. 9,364,106.

(51) Int. Cl.

| | |
|---|---|
| ***A47G 19/02*** | (2006.01) |
| ***B65D 25/04*** | (2006.01) |
| ***G06K 9/00*** | (2006.01) |
| ***G01G 19/414*** | (2006.01) |
| ***G01G 23/36*** | (2006.01) |
| ***G01N 33/02*** | (2006.01) |
| ***B65D 81/18*** | (2006.01) |
| ***A45C 11/00*** | (2006.01) |
| ***B65D 43/02*** | (2006.01) |
| ***G01G 19/00*** | (2006.01) |
| ***G06T 7/62*** | (2017.01) |
| ***G06T 7/90*** | (2017.01) |
| ***G09B 5/04*** | (2006.01) |
| ***G01G 17/00*** | (2006.01) |
| ***A45C 15/00*** | (2006.01) |
| ***A45C 11/20*** | (2006.01) |
| ***G09B 5/00*** | (2006.01) |
| ***G06T 7/50*** | (2017.01) |
| ***G01G 19/56*** | (2006.01) |
| ***G16H 20/60*** | (2018.01) |
| *G01N 21/27* | (2006.01) |

(52) U.S. Cl.

CPC ..... *G06K 9/00201* (2013.01); *G06K 9/00335* (2013.01); *G06T 7/50* (2017.01); *G06T 7/62* (2017.01); *G06T 7/90* (2017.01); *G09B 5/00* (2013.01); *G09B 5/04* (2013.01); *G09B 19/00* (2013.01); *G16H 20/60* (2018.01); *A47G 2200/143* (2013.01); *A47G 2200/166* (2013.01); *A47G 2200/223* (2013.01); *A47G 2200/226* (2013.01); *G01N 21/27* (2013.01); *G01N 2201/12* (2013.01)

(56) References Cited

U.S. PATENT DOCUMENTS

| | | | |
|---|---|---|---|
| 6,600,805 | B2 | 7/2003 | Hansen |
| 7,550,683 | B2 | 6/2009 | Daughtry |
| 7,851,711 | B2 | 12/2010 | Rump |
| 8,345,930 | B2 | 1/2013 | Tamrakar et al. |
| 8,439,683 | B2 | 5/2013 | Puri et al. |
| 8,605,952 | B2 | 12/2013 | Boushey et al. |
| 8,625,889 | B2 | 1/2014 | De Oliveira et al. |
| 8,636,516 | B2 | 1/2014 | Batsikouras |
| 8,770,983 | B2 | 7/2014 | Batsikouras |
| 2002/0027164 | A1 | 3/2002 | Mault et al. |
| 2002/0124017 | A1 | 9/2002 | Mault |
| 2003/0076983 | A1 | 4/2003 | Cox |
| 2009/0288887 | A1 | 11/2009 | Chen |
| 2010/0038149 | A1 | 2/2010 | Corel |
| 2012/0031805 | A1 | 2/2012 | Stolarczyk |
| 2012/0096405 | A1 | 4/2012 | Seo |
| 2012/0135383 | A1 | 5/2012 | Jang et al. |
| 2012/0135384 | A1 | 5/2012 | Nakao |
| 2013/0058566 | A1 | 3/2013 | Sato et al. |
| 2013/0203024 | A1 | 8/2013 | Dekar |
| 2014/0063180 | A1 | 3/2014 | Sharma |

APPARATUS AND METHOD FOR IDENTIFYING FOOD NUTRITIONAL VALUES

CROSS REFERENCE TO RELATED APPLICATIONS

This application is a continuation-in-part utility patent application which claims the benefit to and priority from U.S. patent application Ser. No. 14/636,089 filed on Mar. 2, 2015, and is also a continuation-in-part of U.S. patent application Ser. No. 14/848,992 filed on Sep. 9, 2015.

BACKGROUND

1. Field of the Invention

The present invention relates generally to diet control and nutrition estimation of food. More specifically, the present disclosure is related to a system and method for monitoring nutritional value of food and consumer behavior as it relates to consumer's dietary needs, preferences, and/or medical conditions.

2. Description of Related Art

The total economic impact of poor nutrition has proven difficult to quantify as a whole, with estimates ranging from $70.9B up to as much as $474B according to the USDA's Economic Research Service. There is little doubt that the consequences of poor nutrition in our country are severe. According to the Centers for Disease Control and Prevention (CDC), as of 2010 55% of deaths in the U.S. are from causes linked to poor nutrition and over two thirds of adults over 20 are overweight or obese. Even more concerning is that childhood obesity has more than doubled and quadrupled in adolescents in the past 30 years. The American Diabetes Association (ADA) reports that nearly 26 million Americans (over 11% of the adult population) have diabetes, and 79 million have pre-diabetes, a precursor to the disease. Over 40 percent of diabetics will develop Chronic Kidney Disease, usually within 10 years. The death rate of patients with diabetic nephropathy is high when compared to the general population, with cardiovascular disease killing more than half. The current ADA statistics illustrate that diabetes is prevalent, getting worse, and has perilous implications. Despite increased awareness and better medical treatments, the rate of obesity and diabetes continues to grow around the globe and is expected to double over the next 25 years.

Many recent research studies have shown clear correlations between poor dieting and health conditions. Poor diets, such as over eating, under eating, and/or consuming poor quality food have direct correlations to certain medical conditions, such as diabetes, cancer, heart disease, hypertension, chronic kidney disease, obesity, and the like. For consumers and patients trying to control the quality and habit of consuming food, it is often difficult to identify what kinds of food and eating habits can improve their health condition. It is cumbersome for them to meet their prescribed nutritional requirements or dietary regimen necessary each time they prepare a meal. More importantly, raw ingredients of a meal prior to preparation differ when they are prepared and cooked. Oil, heat, prepping methods and additional cooking ingredients can affect and change the nutritional value of the raw ingredients as they are cooked. Current nutrition information available for ingredients often do not account for the cooking process. Similarly, current available nutrition measuring systems do not account for any additional cooking ingredients that may have been added during the preparation of a meal.

As such, there is a need for an apparatus and method that accounts for additional cooking ingredients and preparation status when measuring the nutritional value of a food item once it is ready to be consumed. In addition, there also is a need for an apparatus and method that enables users to easily interact and follow a daily meal plan which guide them through improving their eating habits. Furthermore, there is a need for an apparatus that can assist with both, pre & post food preparation identification, measurement & analysis.

SUMMARY

The subject matter of this application may involve, in some cases, interrelated products, alternative solutions to a particular problem, and/or a plurality of different uses of a single system or article.

In one aspect, a food container for monitoring a food item being consumed by a user is provided. The food container may comprise, among other things, one or more partitions, a weight sensor, a food identification sensor, and a computerized user interface. The one or more partitions may be formed by the food container to receive and retain the food item. The weight sensor may be positioned within the food container to measure a weight of the food item received by the one or more partitions. The food identification sensor may be positioned by the food container to identify a type of the food item. The one or more processors may be in communication with the weight sensor and the food identification sensor. Based on the information measured by the weight sensor and the food identification sensor, a nutritional value of the food item may be determined. The one or more processors may further be in communication with a storage unit. Lastly, the computerized user interface may display information processed by the one or more processors.

In another aspect, a method for monitoring a food item being consumed by a user is provided. The food item may be received and retained by a food container. The one or more processors may receive a weight of the food item from a weight sensor, where the weight sensor is positioned within the food container to measure the weight of the food item. The type of the food item may be identified with a food identification sensor. The food identification sensor may be positioned to identify a type of the food item. The one or more processors may be in communication with the food identification sensor, the weight sensor, and a storage unit. Finally, the one or more processors may determine a nutritional value of the food item based on the weight and the type of the food item received by the weight sensor and the food identification sensor.

DETAILED DESCRIPTION

Figure 1:
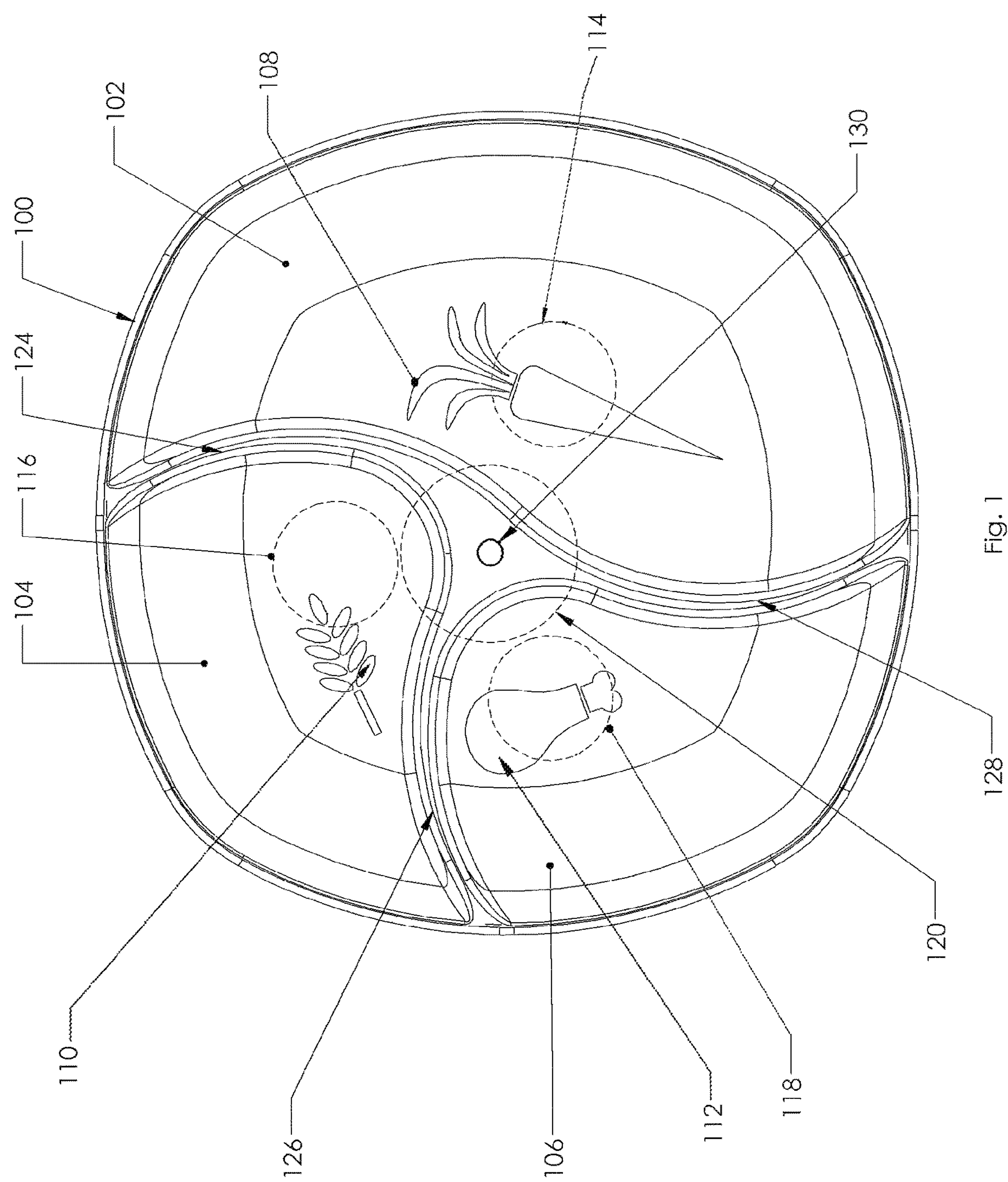
FIG. 1 provides an exemplary embodiment of the food container.

The detailed description set forth below in connection with the appended drawings is intended as a description of presently preferred embodiments of the invention and does not represent the only forms in which the present invention may be constructed and/or utilized. The description sets forth the functions and the sequence of steps for constructing and operating the invention in connection with the illustrated embodiments.

In referring to the description, specific details are set forth in order to provide a thorough understanding of the examples disclosed. In other instances, well-known methods, procedures, components and materials have not been described in detail as not to unnecessarily lengthen the present disclosure.

It should be understood that if an element or part is referred herein as being "on", "against", "in communication with", "connected to", or "coupled to" another element or part, then it can be directly on, against, in communication with, connected or coupled to the other element or part, or intervening elements or parts may be present. When used, term "and/or", includes any and all combinations of one or more of the associated listed items, if so provided.

The terminology used herein is for the purpose of describing particular embodiments only and is not intended to be limiting. As used herein, the singular forms "a", "an", and "the", are intended to include the plural forms as well, unless the context clearly indicates otherwise. It should be further understood that the terms "includes" and/or "including", when used in the present specification, specify the presence of stated features, integers, steps, operations, elements, and/or components, but do not preclude the presence or addition of one or more other features, integers, steps, operations, elements, components, and/or groups thereof not explicitly stated.

Some embodiments of the present invention may be practiced on a computer system that includes, in general, one or a plurality of processors for processing information and instructions, RAM, for storing information and instructions, ROM, for storing static information and instructions, a data storage unit such as a magnetic or optical disk and disk drive for storing information and instructions, modules as software units executing on a processor, an optional user output device such as a display device (e.g., a monitor) for displaying information to the computer user, and an optional user input device.

As will be appreciated by those skilled in the art, the present examples may be embodied, at least in part, a computer program product embodied in any tangible medium of expression having computer-usable program code stored therein. For example, some embodiments described below with reference to flowchart illustrations and/or block diagrams of methods, apparatus (systems) and computer program products can be implemented by computer program instructions. The computer program instructions may be stored in computer-readable media that can direct a computer or other programmable data processing apparatus to function in a particular manner, such that the instructions stored in the computer-readable media constitute an article of manufacture including instructions and processes which implement the function/act/step specified in the flowchart and/or block diagram. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

In the following description, reference is made to the accompanying drawings which are illustrations of embodiments in which the disclosed invention may be practiced. It is to be understood, however, that those skilled in the art may develop other structural and functional modifications without departing from the novelty and scope of the instant disclosure.

Generally, the present invention concerns an apparatus and method for monitoring a nutritional value of a food item. The apparatus and method may comprise a food container to receive and retain the food item. One or more weight sensors may measure weight of the food item being placed in the food container. Based on the measured weight and the identification of the food item, a nutritional value of the food item can be identified and notified to a user. The apparatus may further comprise a food identification sensor to identify a type of the food item. In one embodiment, the food identification sensor may be a camera which captures an image of the food item, in turn, one or more processors may identify the type of the food item based on the image. The method may be carried by a system comprising the apparatus and the one or more processors, which may provide various functions based on the data gathered by the apparatus and system. The user behavior of food consumption, such as calories intake and eating habit may be monitored and evaluated by the apparatus, in order to improve the user's nutritional intake. The apparatus may also provide a meal plan either based on the food item being consumed by the user over time or an input from the user.

Storage unit contemplated herein may be in various file format including, but are not limiting to, XML, JSON, CSV, binary, over any connection type: serial, Ethernet, etc. over any protocol: UDP, TCP, and the like.

Computer or computing device contemplated herein may include, but are not limited to, virtual systems, Cloud/remote systems, desktop computers, laptop computers, tablet computers, handheld computers, smart phones and other cellular phones, and similar internet enabled mobile devices, digital cameras, a customized computing device configured to specifically carry out the methods contemplated in this disclosure, and the like.

Network contemplated herein may include, for example, one or more of the Internet, Wide Area Networks (WANs), Local Area Networks (LANs), analog or digital wired and wireless telephone networks (e.g., a PSTN, Integrated Services Digital Network (ISDN), a cellular network, and Digital Subscriber Line (xDSL)), radio, television, cable, satellite, and/or any other delivery or tunneling mechanism for carrying data. Network may include multiple networks or sub-networks, each of which may include, for example, a wired or wireless data pathway. The network may include a circuit-switched voice network, a packet-switched data network, or any other network able to carry electronic communications. Examples include, but are not limited to, Picture Transfer Protocol (PTP) over Internet Protocol (IP), IP over Bluetooth, IP over WiFi, and PTP over IP networks (PTP/IP).

Weight sensors contemplated herein may measure weight of the food item in various ways which may include, but are not limited to, electrically resistive strain gauges, force sensitive resistors, photoelectric weight sensors, hydraulic weight sensors, pneumatic weight sensors, and the like.

Camera contemplated herein may include, but are not limited to, DSLR, non-SLR digital cameras (e.g., but not limited to, compact digicams and SLR-like bridge digital cameras (also known as advanced digital cameras), and SLR-like interchangeable lens digital cameras), as well as video recorders (e.g., but not limited to, camcorders, analog cameras and IP cameras, and the like; a device that can provide a video feed of any duration, such as a DVR; a portable computing device having a camera, such as a tablet computer, laptop computer); and the like.

System and method for identifying, measuring and analyzing food nutritional values and consumer eating behaviors is provided. The system may comprise a food container, one or more weight sensors, one or more food identification sensors, a computerized system with one or more processors, a computerized user interface, and a storage unit accessible by the one or more processors via a network. In general, the system may comprise one or more computers or computerized elements in communication working together to carry out the different functions of the system provided herein. The invention contemplated herein may further comprise a non-transitory computer readable media configured to instruct a computer or computers to carry out the steps and functions of the system and method, as described herein. In some embodiments, the communication among the one or more computers or the one or more processors alike, may support a plurality of encryption/decryption methods and mechanisms of various types of data.

The computerized user interface may be comprised of one or more computing devices in networked communication with each other. The computer or computers of the computerized user interface contemplated herein may comprise a storage unit or a memory, a processor, and input/output system. In some embodiments, the computer may further comprise a networked connection and/or a display. These computerized elements may work together within a network to provide functionality to the computerized user interface.

The computerized user interface may be any type of computerized interfaces known in the art capable of allowing a user to input data and receive a feedback therefrom. Data input may include user information, ingredients, recipes, meal plans, user health conditions, user dietary requirements and the like. The computerized user interface may further provide outputs including rapid eating warnings, portion control warnings, type of food item, nutritional value of food item, and meal plan recommendations.

A food container for monitoring nutritional value of a food item may comprise a body, where the body may form one or more partitions to receive and retain the food item being consumed by a user. Each of the one or more partitions may receive different types of food items which are to be consumed by the user. The food items may be in any form including, but not limited to, liquid, solid, powder, gas, and the like. Each of the one or more partitions may be defined by a wall and the body, compartmentalizing the food container in one or more partitions. The wall may be repositionable to adjust the configuration and/or size of the one or more partitions.

In one embodiment, the food container may house a plurality of weight sensors. Each of the plurality of weight sensors may be positioned to measure the weight of the food item being retained and received by each of the one or more partitions formed by the body. The plurality of weight sensors may be in electronic communication with one or more processors via a network. A weight measured by each of the plurality of weight sensors may be transmitted to the one or more processors for further evaluation and monitoring of the food item.

In some embodiments, the food container may house a single weight sensor measuring the weight of the food item being placed in the plurality of partitions. The food items being retained by each of the plurality of partitions may be weighed by the single weight sensor accumulatively. Similarly, the food container may comprise a single partition and a single weight sensor to measure the weight of the food item being retained by the single partition.

In some embodiments, the plurality of weight sensors may be repositioned as the configuration of the plurality of partitions are rearranged.

In some embodiments, weights measured from the plurality of weight sensors may be combined to identify a total weights of the food item retained by the one or more partitions.

The food container may further comprise a food identification sensor. The food identification sensor may be positioned by the food container to identify the type of food item being retained by the one or more partitions. The information obtained from the food identification sensor may be communicated to the one or more processors to determine the type of food being retained by the one or more partitions. In some embodiments, the food identification sensor may gather information regarding the properties of the food item to identify the type of the food item. The properties of the food item may include visual elements, such as volume, texture, color, spectrum, shape, and the like. The properties of the food item may also include non-visual elements, such as, temperature, chemical composition, food composition, and the like. Based on the information received from the food identification sensor, the one or more processors may then identify the food item retained by the one or more partitions. The one or more processors may be in communication with the storage unit, where various types of food items may be linked to their corresponding properties expected from each of the various types of food item.

In one embodiment, the food identification sensor may be a camera. The food container may further comprise a camera positioned to capture an image which includes at least a portion of the food item being retained within each of the one or more partitions. The captured image may be further analyzed by the one or more processors to identify the type of the food item.

In some embodiments, the one or more processors may be in communication with the storage unit where it stores a database of images of food items, which can be compared with the captured image to identify the type of the food item. For example, the images may be compared pixel-to-pixel to approximate the type of the food item.

In some embodiments, the one or more processors may compare the captured image to the database to identify the type of the food item. The storage unit may have a database which stores information that links properties of the food item to the type of food item. By way of an example, visual properties such as, color, shape, and texture of strawberries may be matched with the image to identify that the image captured is a strawberry.

In some embodiments, the food item may be a mixture of various ingredients. In this embodiment, the type of the food item may be identified by individually identifying each of the various ingredients of the food item, as well as collectively identifying the overall properties of the food item. The one or more processors may be in communication with a database which stores information that links various ingredients to a matching type of food item. By way of an example, pasta often includes a variety of ingredients. By analyzing an image of the pasta which would include the variety of ingredients, the one or more processors would identify that the food item being retained by the food container is a pasta made with the variety of ingredients identified from the image.

In some embodiment, the additional cooking ingredients may be identified from various image analyzing techniques as described above. The one or more processors may approximate the additional cooking ingredients, such as oil and spices based on the type of the food item.

In some embodiments, a plurality of cameras may be positioned to each capture at least a portion of each of the food items being retained by each of the one or more partitions.

In some embodiments, each of the plurality of cameras may be positioned at the wall facing each of the one or more partitions outwardly away from the center of the food container.

In some embodiments, the camera may tilt and/or rotate to capture the image of the food item at a desired angle and/or proximity. The one or more processors may control movement of the camera to capture the image of the food item at the desired angle. The camera may be operated by the user via the computerized user interface. Similarly, the operation of the camera may be automated to capture the image of the food item.

In some embodiments, the camera may be capable of auto focusing.

In some embodiments, the camera may observe the food item and any movement in the vicinity of the food item to monitor an eating habit of the user. The eating habit may include the speed in which the user consumes the food item, the frequency in which the user consumes a certain category of food, the amount of the food the user consumes in each intake or during the meal, and the like. The eating habit may be monitored to identify any pattern and behavior.

In some embodiments, the camera may be in communication with the one or more processors to identify the user utilizing the food container. The system may employ a face recognition protocol to identify the image of the user's face via the camera. Once the user is identified, a meal plan or recommended settings corresponding to the user may be determined by the one or more processors.

The one or more processors with the camera may further determine a volume of the food item placed in the one or more partitions.

In one embodiment, based on the type and the weight of the food item in the instant image, the volume may be estimated. The database may store type-to-density information which entails densities of the various food types. With the known weight and known density, the volume of the food item may be identified. The nutritional value of the food item may be determined based on the identified volume of the food item and its type.

In some embodiments, the volume of the food item may be approximated based on a surface area of the food item (for example, the number of pixels of the food item that occupies the instant image). In some embodiments, the volume of the food item may be identified based on two or more instant images of the same food container taken at varying angles. The volume of the food item may be approximated by a three-dimensional reconstruction model of the food item based on the two or more instant images. In some embodiments, the volume may be computed based on a three-dimensional model of the food item obtained from a multi-view geometry from two or more images of the food item. A three-dimensional shape reconstruction can be applied with two or more images to estimate the volume of the food item.

In some embodiments, the camera may be a depth-sensing camera that can identify a depth of the food item. In some embodiments, the depth of the food may be identified from a multiple positions of the food item, especially if the food item has an irregular depth profile. By identifying the depth of the food item, a depth profile of the food item may be built by the one or more processors. Thus, the one or more processors may determine the volume of the food item. With the type-to-density information stored in the database, a weight of the food item may be derived based on the known volume and the type. As such, in some embodiments, the weight sensor may not be necessary to discover the weight of the food item. These and other techniques of computer vision methods may be applied to estimate the volume of the food item.

In another embodiment, the food identification sensor may be a surface sensor. The surface sensor may be positioned by the food container to analyze the composition of the food item being retained by the one or more partitions. The surface sensor may identify composition of the food item in various ways. By way of example, the surface sensor may be a Surface Plasmon Resonance (SPR). The SPR may identify the type, the preparation status, and the additional cooking ingredients of the food item. By way of another example, the surface sensor may be a spectrometer capable of detecting pesticide, allergen, chemical compositions, food composition, pathogen, and the like from the surface of the food. The spectrometer may identify the type, the preparation status, and the additional cooking ingredients of the food item by analyzing the spectrum. Based on the composition of the food item, the one or more processor may identify the type, the preparation status, and the additional cooking ingredients of the food item.

The spectrometer may be used with an optical system, such as the camera. The camera may be used with the spectrometer to identify the type and/or the preparation status of the food item.

The present system may employ various types of spectrometers capable of identifying material using a spectral analysis, including but not limiting to, imaging spectrometer, spectroscopic apparatus and techniques, spectrometric apparatus and techniques, spectrometry, spectral imaging techniques, multispectral imaging spectrometer, hyperspectral imaging spectrometer, nuclear magnetic resonance (NMR), infrared (IR), near-infrared (NIR), UV-VIS spectroscopy, fluorescence, mid-infrared (MIR), Raman spectroscopy, and other spectroscopy.

The spectrometer may utilize a wide range of spectral bands, including UV, VIS or IR rays and the fluorescence. For example, a hyperspectral imaging spectrometer is a sensor that creates a complete picture of the environment or various objects, each pixel containing a full visible, VNIR, NIR, ultraviolet, or infrared spectrum. The spectrometer may also image narrow bands of light, for example a hyperspectral imaging spectrometer.

In addition to identifying the food composition of the food item, the spectrum may examine the quality of the food item.

In a further embodiment, the food identification sensor may detect the temperature of the food item. The type and/or the preparation status of the food item may be determined based on the temperature identified by the food identification sensor. In this embodiment, the temperature of the food item may be detected by a heat sensor.

In yet another embodiment, the information obtained by the food identification sensor may be further processed to identify a preparation status of the food item. The ingredient of the food item once cooked may change its volume, texture, spectrum, chemical composition, color, shape, temperature, and the like. The preparation status of the food item may be determined based on the information identified by the food identification sensor. By way of example, when food is cooked the color of the food tends to change. By recognizing the color of the food item from the image, the preparation status of the food item may be identified.

The system and method for identifying, measuring and analyzing food nutritional values and consumer eating behaviors may further comprise an identification module. Similar to the face recognition by the camera, the identification module may verify the patient's identity by observing individually unique biological and/or physiological signature of the use, for example, finger prints are unique biological and physiological signature of individuals.

The apparatus and system for identifying, measuring and analyzing food nutritional values and consumer eating behaviors may further comprise an optical scanner to identify the type of the food item being retained by the one or more partitions. The optical scanner may be positioned to read an item identifier affixed to the food item which indicates the type of food item. The optical scanner may include, but are not limited to, a camera, a barcode scanner, and the like. Once the item identifier is read by the optical scanner, the item identifier may be compared and matched to an identifier-to-type list stored in the storage unit. The identifier-to-type list may include list of food types each corresponding to an item identifier. In some embodiment, the camera positioned to identify the type and the preparation status of the food item may be further utilized as the optical scanner.

The food container may further be in communication with a computerized user interface for the user to interact and control the operation of the food container, the system, and its components. The computerized user interface may display any input and output derived from the components of the system. The data processed by the one or more processors may be displayed by the computerized user interface.

In one embodiment, the computerized user interface may indicate the weight of the food item through a display. The weight measured by the weight sensors may be displayed.

In another embodiment, the computerized user interface may indicate the type of the food item determined by the one or more processors based on the information obtained by the food identification sensor.

In yet another embodiment, the computerized user interface may indicate the preparation status of the food item determined by the one or more processors based on the information obtained by the food identification sensor.

In a further embodiment, the computerized user interface may indicate a nutritional value of the food item. The one or more processors may determine the nutritional value of the food item based on the information obtained from the weight sensor and the food identification sensor. The nutritional value may further be determined by the one or more processors based on the preparation status identified by the food identification sensor.

The computerized user interface may be configured to receive an input from the user. The computerized user interface may receive inputs from the user regarding their dietary requirements, such as a health condition, food allergy information, and the like. The input received from the user may further be communicated to the one or more processors to further evaluate and monitor the nutritional value of the food item and the eating habit of the user. The eating habit may include the speed in which the user consumes the food item, the frequency in which the user consumes a certain category of food, the amount of the food the user consumes in each intake or during the meal, and the like. The eating habit may be monitored to identify any pattern and behavior. The one or more processors may provide a recommended meal plan suitable to the user based on the user input. The user input may be in any form including, but not limited to, text input, audible input, and the like.

The computerized user interface may provide the user an alert issued by the one or more processors. The alert being issued by the one or more processors may be in any form. The alert may be a visual alarm, such as light or other visual signals presented by the computerized user interface. The alert may be an audible alarm. The alert may be an alert message presented on the computerized user interface. The alert may be issued when the measured data exceeds an expected data. The expected data may be stored in the storage unit. The expected data may vary per the user due to the various meal plans, health conditions, dietary requirements, food allergy information, eating behaviors, and the like which are recommended to improve the user's health. The expected data also may be inputted by the user via the computerized user interface.

In one embodiment, the alert may be issued based on a food intake speed which represents the speed in which the user consumes the food item placed in the one or more partitions. The one or more processors may compare the food intake speed measured to an expected food intake speed and issue the alert when the food intake speed exceeds the expected food intake speed. In one embodiment, the food intake speed may be identified based on the change in the weight of the food item as they are consumed by the user. The weight of the food item may be monitored by the one or more processors in communication with the weight sensor. In another embodiment, the food intake speed may be identified by a motion monitoring unit. The food container may further comprise the motion monitoring unit. The motion monitoring unit may be positioned to observe the movement of the user in the vicinity of the food item as the user consumes the food item. The motion monitoring unit may be in communication with the one or more processors. The motion monitoring unit may include, but is not limited to, an accelerometer, a gyroscope, and the like. The motion monitoring unit may be utilized to monitor the movement of the user within the vicinity of the food container.

In another embodiment, the alert may be issued based on a portion of which the user consumes the food item at each intake. When the user consumes the food item in a portion bigger than an expected amount at a time, the alert may be issued to alert the user that the user should take a smaller portion at one time. The frequency may be monitored by the motion monitoring unit in combination with the monitoring of the weight of the food item as they are consumed by the user.

In yet another embodiment, the alert may also be issued based on the nutritional value of the food item being placed in the one or more partitions. The one or more processors may issue the alert when the nutritional value of the food item being placed in the one or more partitions exceeds an expected nutritional value. The nutritional value of the food item may be determined based on the information received from the weight sensor and the food identification sensor. In addition, the nutritional value also may be determined based on the additional cooking ingredients, such as oil, spices, and the like. The nutritional value may include, but is not limited to, the total calories of the food item, the total calories from various food categories (for example, carbohydrates, fat, protein, and the like), and other nutritional information.

The alert methods described herein may be modified to provide alerts at a various situations. For example, the alert may be issued when the expected data (i.e. the expected nutritional value, the expected amount, the expected weight, the expected food intake speed, and the like) is not met, exceeded, met, and the like. These and other various scenarios would be apparent to those having ordinary skill in the art.

In a further embodiment, the type and the preparation status of the food item may be inputted by the user. The computerized user interface may receive input from the user which may be in communication with the one or more processors.

The computerized user interface may provide the user with a meal plan or dietary recommendations. The one or more processors may be in communication with a storage unit that stores information related to meal plans and dietary recommendations. The one or more processors may relay such information to the computerized user interface for the user to follow. The dietary recommendations and the meal plan may be optimized based on the user's health conditions, dietary requirements, food allergy information, and the like. In some embodiments, the user may provide the user input via the computerized user interface prior to utilizing the food container and its functions. The user input may include the health conditions, dietary requirements, and the like, based on which the meal plan and/or dietary recommendations can be determined by the one or more processors. By way of example, the user having certain medical conditions may require a low carbohydrate diet. The one or more processors may receive such requirement by the user and provide the meal plan suitable to the requirement. The expected data may be adjusted accordingly to provide alert at a suitable condition.

The one or more processors may track the food item, the nutritional value, and various eating behaviors available by the present invention over time. The storage unit may store the tracked information overtime. In light of the tracked information, the one or more processors may recommend a meal plan that may benefit the user's health or comply to the user input.

The system for identifying, measuring and analyzing food nutritional values and consumer eating behaviors may comprise one or more computerized elements working collectively within a network. The system may comprise the food container, the one or more processors, and the storage unit, all of which are in direct or indirect communication with one another via the network. The system may comprise one or more computing devices which may employ the functions disclosed herein. In some embodiments, the user may utilize a user computing device, such as a smart phone to provide the user input or receive information processed by the one or more processors. The user computing device also may be the computerized user interface to communicate with the system components.

The method for monitoring nutritional value of a food item is provided. The method may be employed by the system and apparatus provided above, and may comprise the process and interaction among the components of the system provided above to carry out different functions described herein.

Generally, the one or more processors receive information from the weight sensor located within the food container and the food identification sensor positioned to identify the type of the food item. Based on the information received by the one or more processors from the weight sensor and the food identification sensor (for example, the type and the preparation status), the nutritional value may be obtained and tracked over time. The nutritional value may be utilized to identify user's eating behaviors and patterns. The behavior and pattern of the user's eating habits may also be applied in various time scale, for example, instant, daily, weekly, and the like. In connection with the type of food item being recognized by the system, a meal plan may be recommended to the user. Alternatively, the meal plan may be predetermined and inputted by the user.

In one embodiment, the method provided herein may determine the nutritional value of the food item based on any combination of the weight, the type, and the preparation status of the food item. The one or more processors may receive the weight of the food item from the weight sensor. It may further receive the type and preparation status of the food item identified by the food identification sensor. The nutritional value of the food item may be determined by the one or more processors knowing the weight of the food item and the type. The one or more processors may be in communication with the storage unit where information regarding conversion of weight of the food item to nutritional value per the type of the food item may be stored. The storage unit may provide information such as composition of each food categories with a food item, conversion rate of weight to calories, and the like.

In another embodiment, the one or more processors may further determine the preparation status of the food item based on the information received by the food identification sensor. The preparation status may factor into determining the nutritional value of the food item. Similarly, the one or more processors may further determine the additional cooking ingredients of the food item based on the information received by the food identification sensor. The additional cooking ingredients may be identified by the food identification sensor or approximated by the one or more processors based on the information gather by the food identification sensor. In some embodiments, the additional cooking ingredients may be approximated based on the preparation status. By way of examples, the preparation status may include steamed, fried, grilled, and the like, depending on the preparation status the additional cooking ingredients such as oil can be approximated. The additional cooking ingredients may further contribute in determining the nutritional value of the food item.

In yet another embodiment, the one or more processors in communication with the storage unit may further track the nutritional value being consumed by the user over time. The tracked nutritional value may be stored in the storage unit. Similarly, the users' eating behavior such as the food intake speed and frequency observed over time may be store in the storage unit. Based on the tracked information available in the storage unit, the recommended meal plan may be determined by the one or more processors. The recommended meal plan may include adjustment in the expected data for the various alert being issued by the one or more processors.

In a further embodiment, the one or more processors may display information processed by the one or more processors using the computerized user interface or the user computing device.

Turning now to FIG. 1, FIG. 1 shows an exemplary embodiment of the food container. In this exemplary embodiment, the food container 100 comprises three partitions 102 104 106 formed to receive and retain the food item in each of the three partitions. The three partitions are defined by the body of the food container and the wall 124 126 128. Each of the three partitions may provide indications to receive and retain certain categories of food such as meat 112, carbohydrates 110, and vegetables 108. A plurality of weight sensors 114 116 118 may each be placed within the food container 100, positioned to measure the food item being retained by each of the three partitions. At around the center of the food container 120, the one or more processors and other circuitry components necessary to provide the methods described herein may be embedded therein. The optical scanner 130 may be positioned to face generally upwards such that the item identifier of the food item may be scanned as the food item is placed in one of the three partitions.

Figure 2:
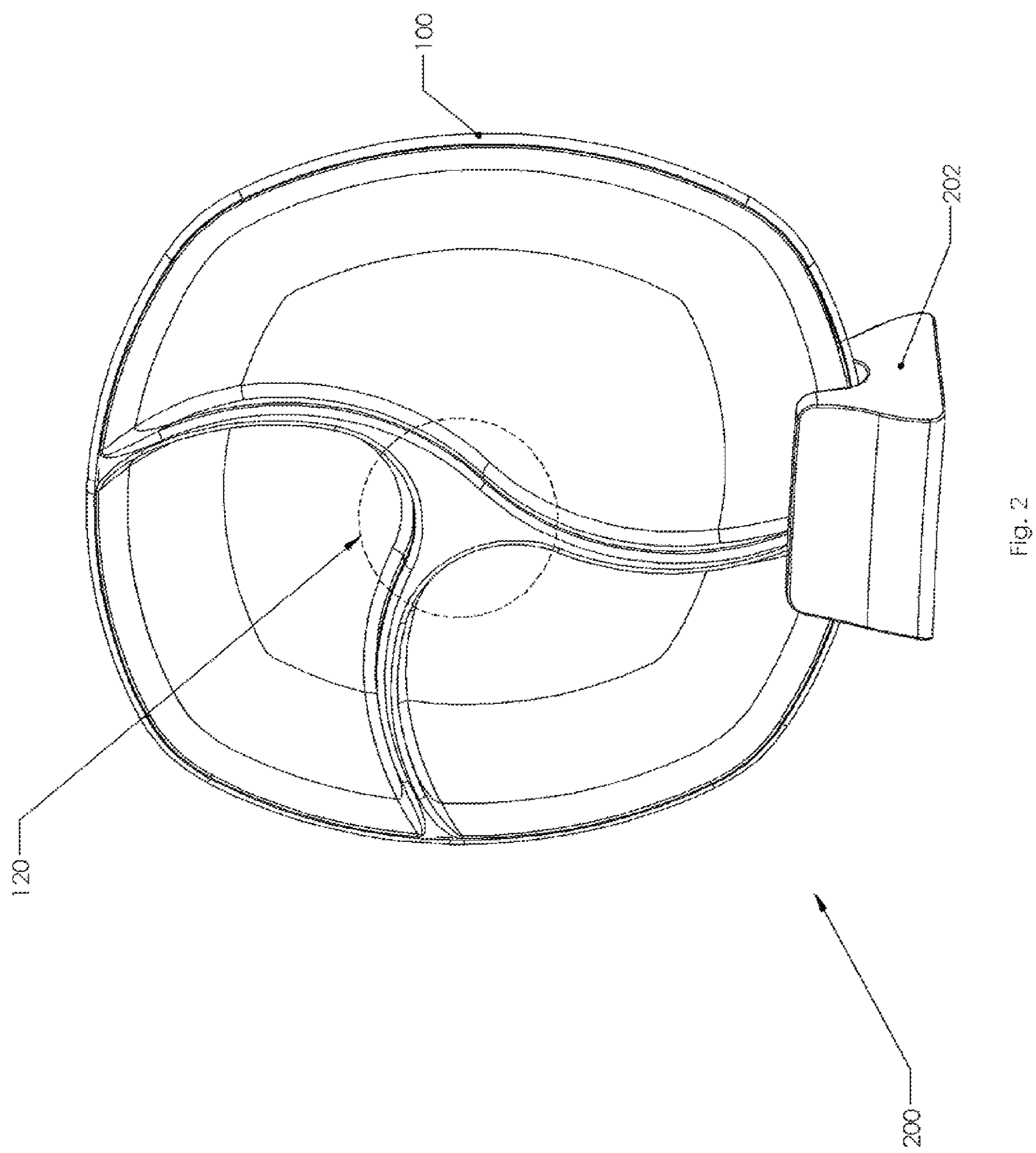
FIG. 2 provides an exemplary embodiment of the food container showing a battery charger.

FIG. 2 describes an exemplary embodiment of the food container showing a battery charger. In this embodiment 200, the battery of the food container 100 may be positioned at the center of the food container 120 and may be rechargeable by the charger 202.

Figure 3:
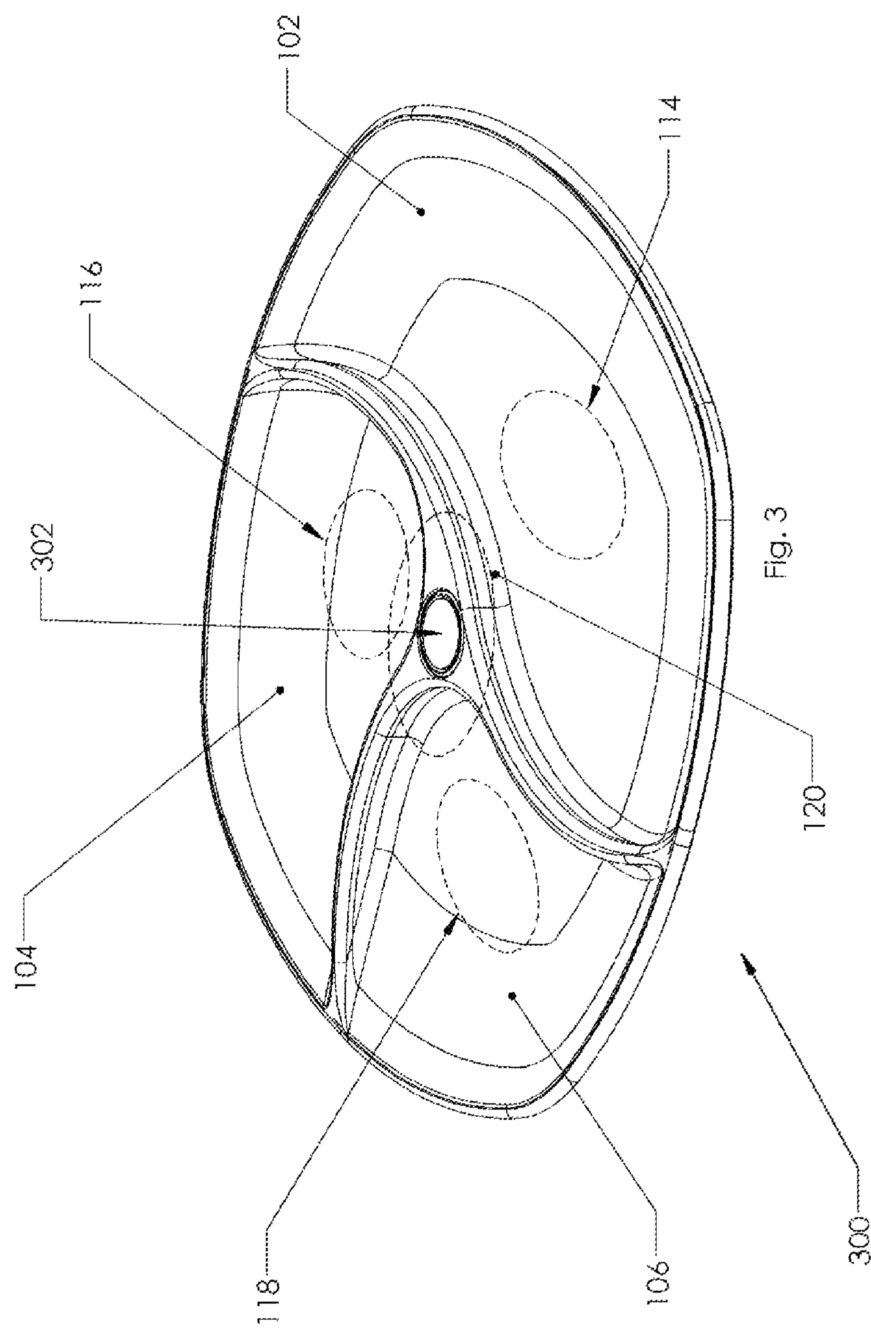
FIG. 3 provides another exemplary embodiment of the food container.

FIG. 3 describes another exemplary embodiment of the food container. In this exemplary embodiment, the food container 300 comprises three partitions 102 104 106 formed to receive and retain the food item. It further comprises the computerized user interface 302 and three weight sensors 114 116 118 positioned to measure weight of the food item being retained by each of the three partitions. A processor may be placed within the center 120 of the food container communicating with the computerized user interface 302. Further, the processor may be in further communication with each of the three weight sensors to receive weight of the food item measured at each of the three partitions.

Figure 4:
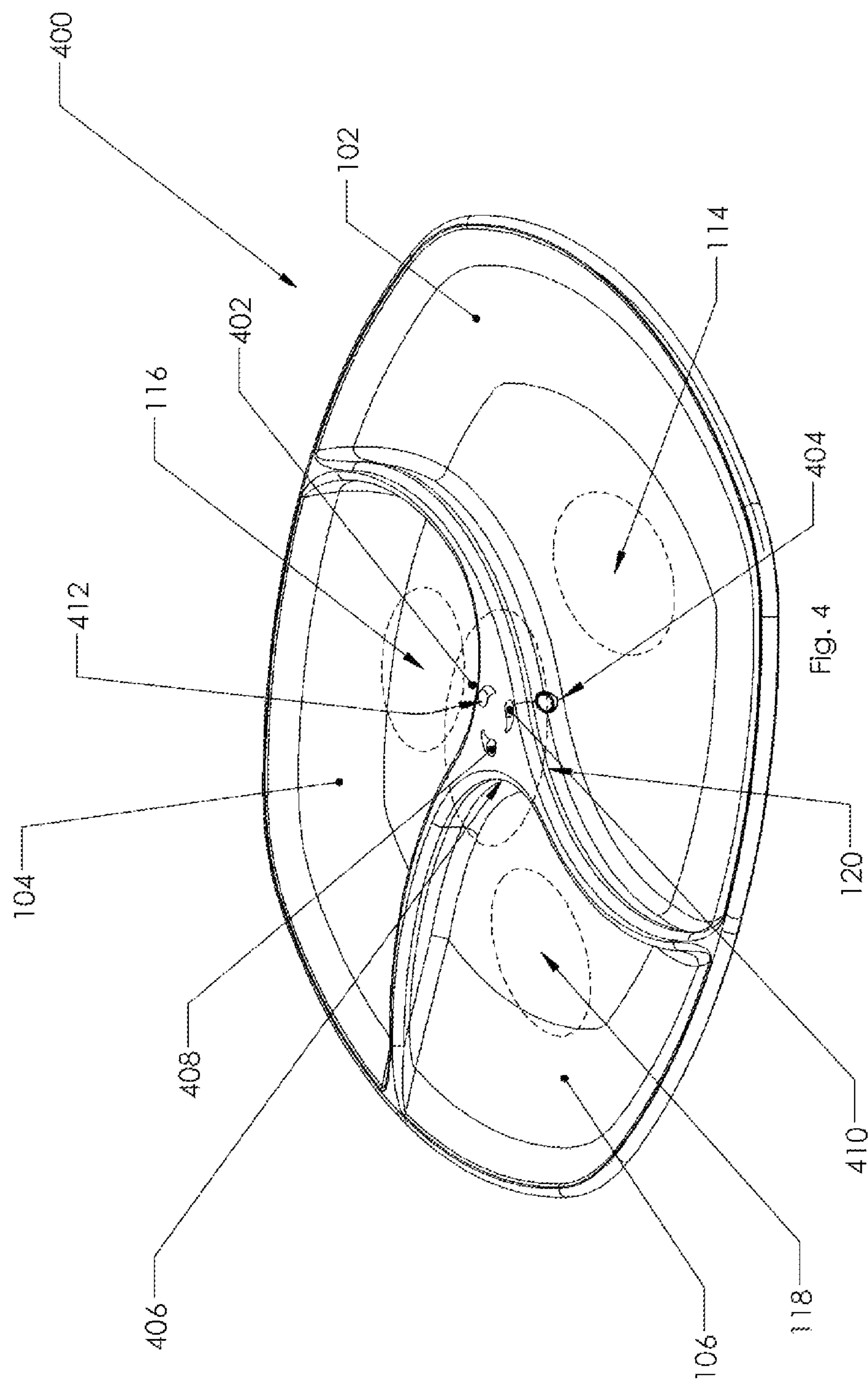
FIG. 4 provides another exemplary embodiment of the food container.

FIG. 4 provides another exemplary embodiment of the food container. The food container 400 comprises three computerized user interfaces in the form of LED lights 408 410 412. Each of the LED lights may be utilized to individually provide alert to the user as each of the three partitions 102 104 106 receives the food item. Three cameras 402 (not visible) 404 (not visible) 406 may each be positioned to capture images of the food item retained by each of the three partitions. Based on the information obtained by each of the three cameras and each of the three weight sensors 114 116 118, the nutritional value of the food item may be provided to the user via the user computing device (not shown). The one or more processors may be placed within the center 120 of the food container 400 communicating information processed by the one or more processors to the user computing device.

Figure 5:
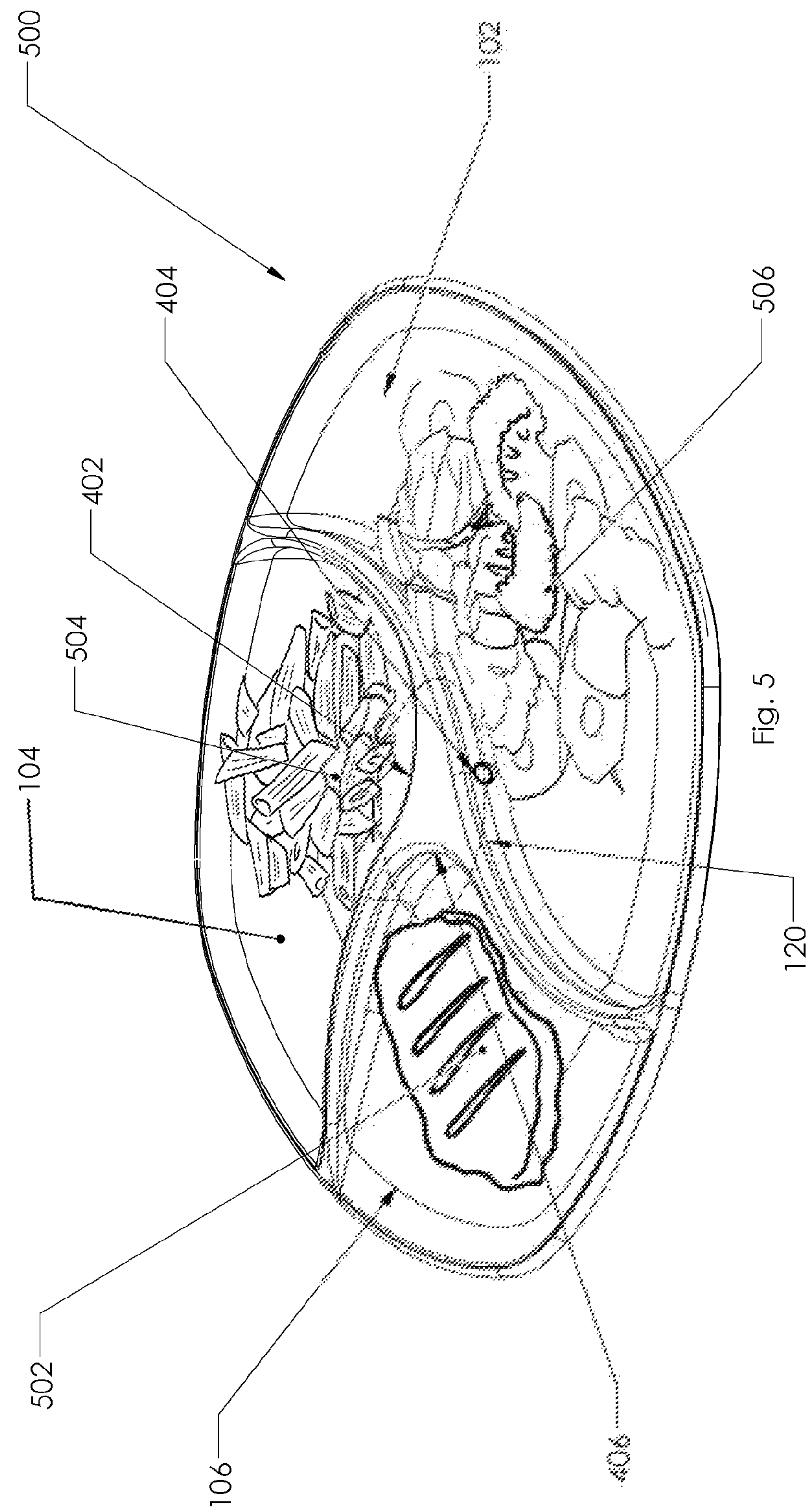
FIG. 5 provides an exemplary embodiment of the food container retaining the food item.

FIG. 5 shows an exemplary embodiment of the food container retaining the food item. In this exemplary embodiment 500, the food items 502 504 506 may be received and retained by each of the three partitions 102 104 106. The one or more processors located within the center 120 of the food container is in communication with each of the three cameras 402 (not visible) 404 (not visible) 406. Each of the three cameras captures the image of the food items 502 504 506, which are then received by the one or more processors to identify the type of each of the food items.

Figure 6:
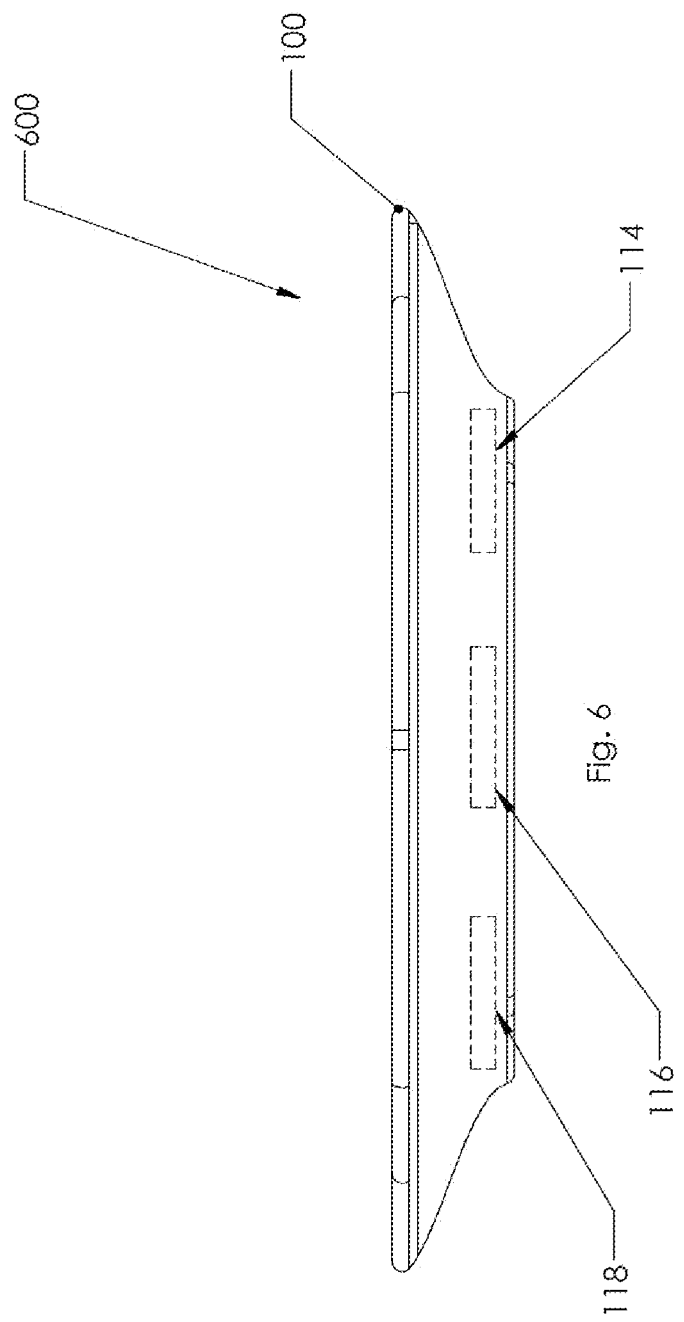
FIG. 6 provides an exemplary locations of the weight sensors.

FIG. 6 shows an exemplary locations of the weight sensors. In this example 600, the three weight sensors 114 116 118 are positioned near at the bottom of the food container 100, measuring the weight of the food item retained by the food container having three partitions.

Figure 7:
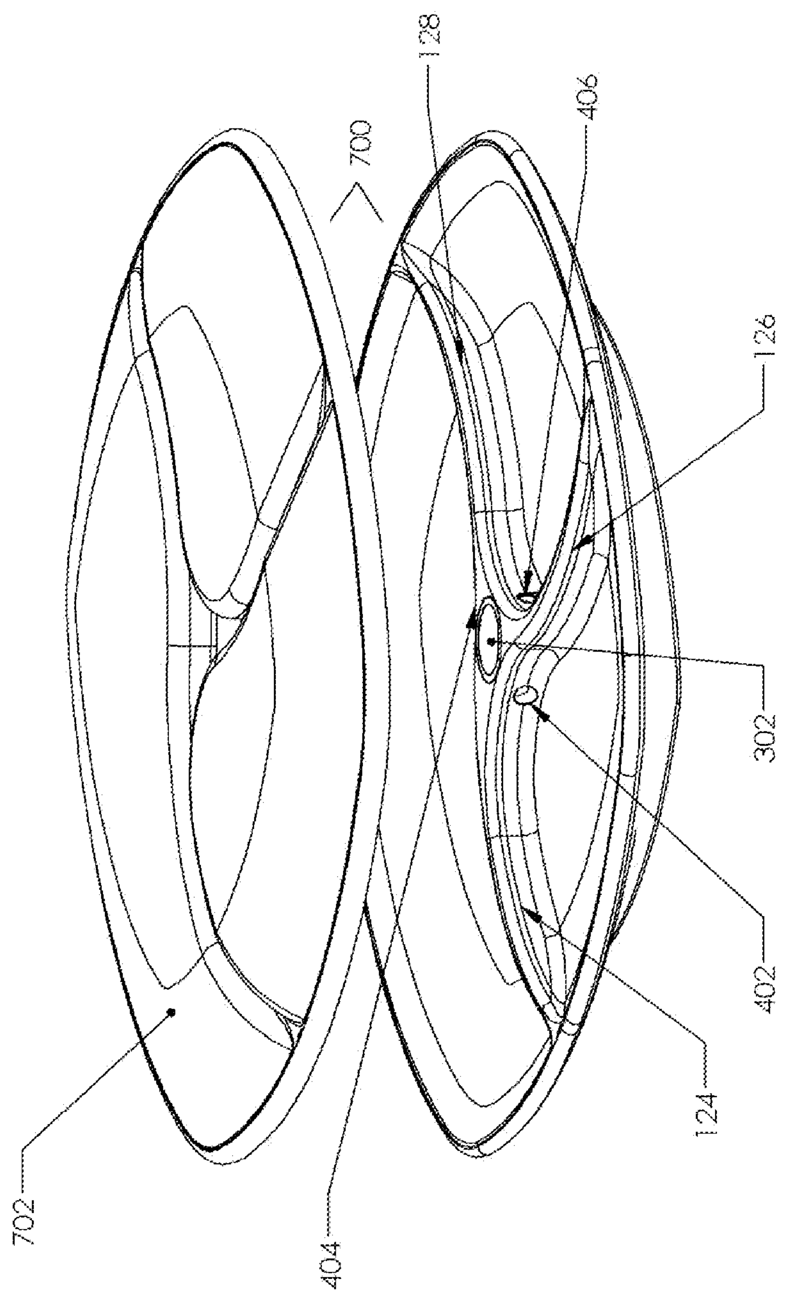
FIG. 7 provides an exemplary embodiment of the food container with the detachable lid.

FIG. 7 describes an exemplary embodiment of the food container with the detachable lid. In this embodiment 700, the detachable lid 702 may be formed to fit and seal the food container. The detachable lid is formed to seal each of the three partitions divided by the wall 124 126 128 individually to prevent food items contained in each of the three partitions from mixing. The detachable lid 702 may be transparent such that the food items retained by the food container and the computerized user interface 302 are visible to the user when the detachable lid 702 is engaged to seal the food item in the food container. The detachable lid and the food container 700 may be microwaveable. The three cameras 402 404 406 are shown.

Figure 8:
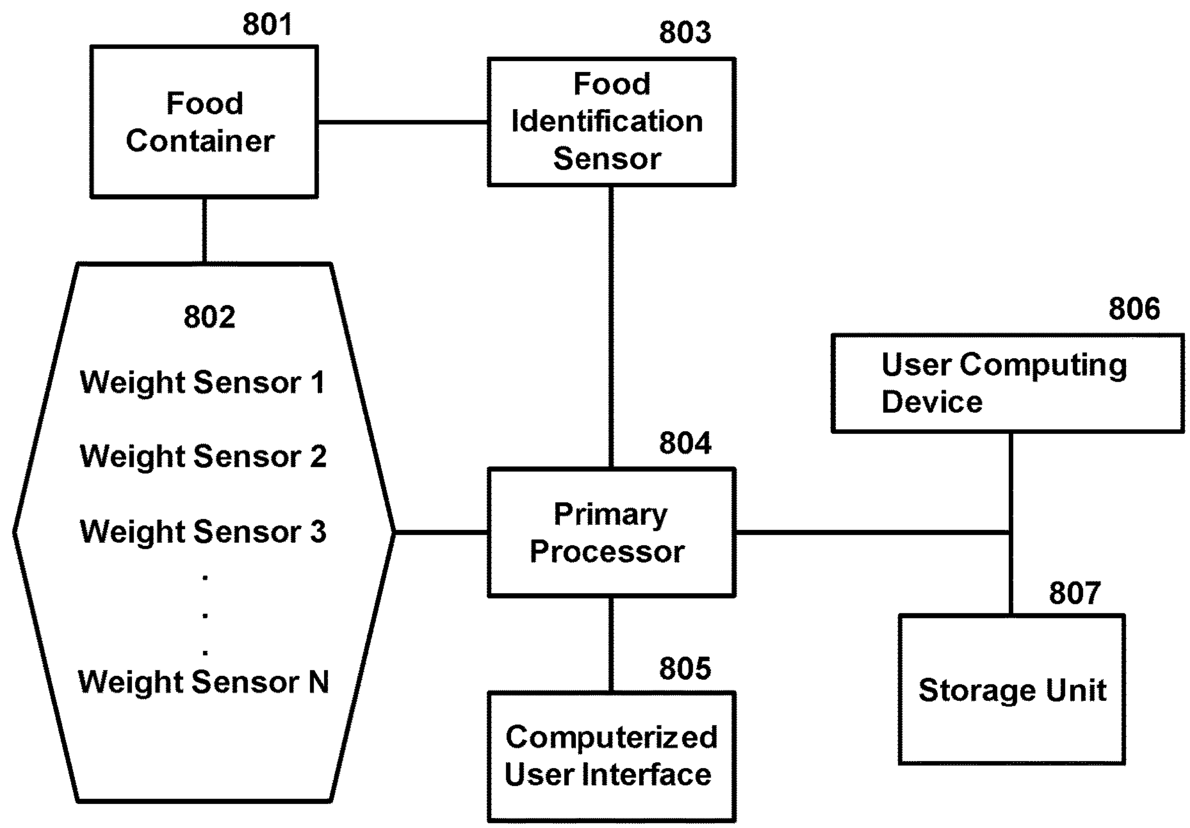
FIG. 8 provides a block diagram describing the system for monitoring nutritional value of food item.

FIG. 8 provides a block diagram describing the system for monitoring nutritional value of food item. The system may comprise the food container 801 having a plurality of weight sensors 802. Each of the plurality of weigh sensors 802 may be positioned within the food container 801, each positioned to measure food item being retained by each of the plurality of partitions. The plurality of weight sensors 802 measure weight of the food item retained by each of the plurality of partitions. The information obtained by the plurality of weight sensors may be communicated to the primary processor 804. The food identification sensor 803 may obtain information to identify type of the food item. The primary processor may determine the type of the food item based on the information obtained by the food identification sensor 803. The primary processor may further be in communication with the computerized user interface 805 displaying the nutritional value calculated by the primary processor, and receiving the user input. In this networked environment, the storage unit 807 may be in communication with the primary processor to provide the expected data to compare with the nutritional value. The user computing device 806 may further be in communication with the primary processor to allow the user to interact with the system provided herein.

Figure 9:
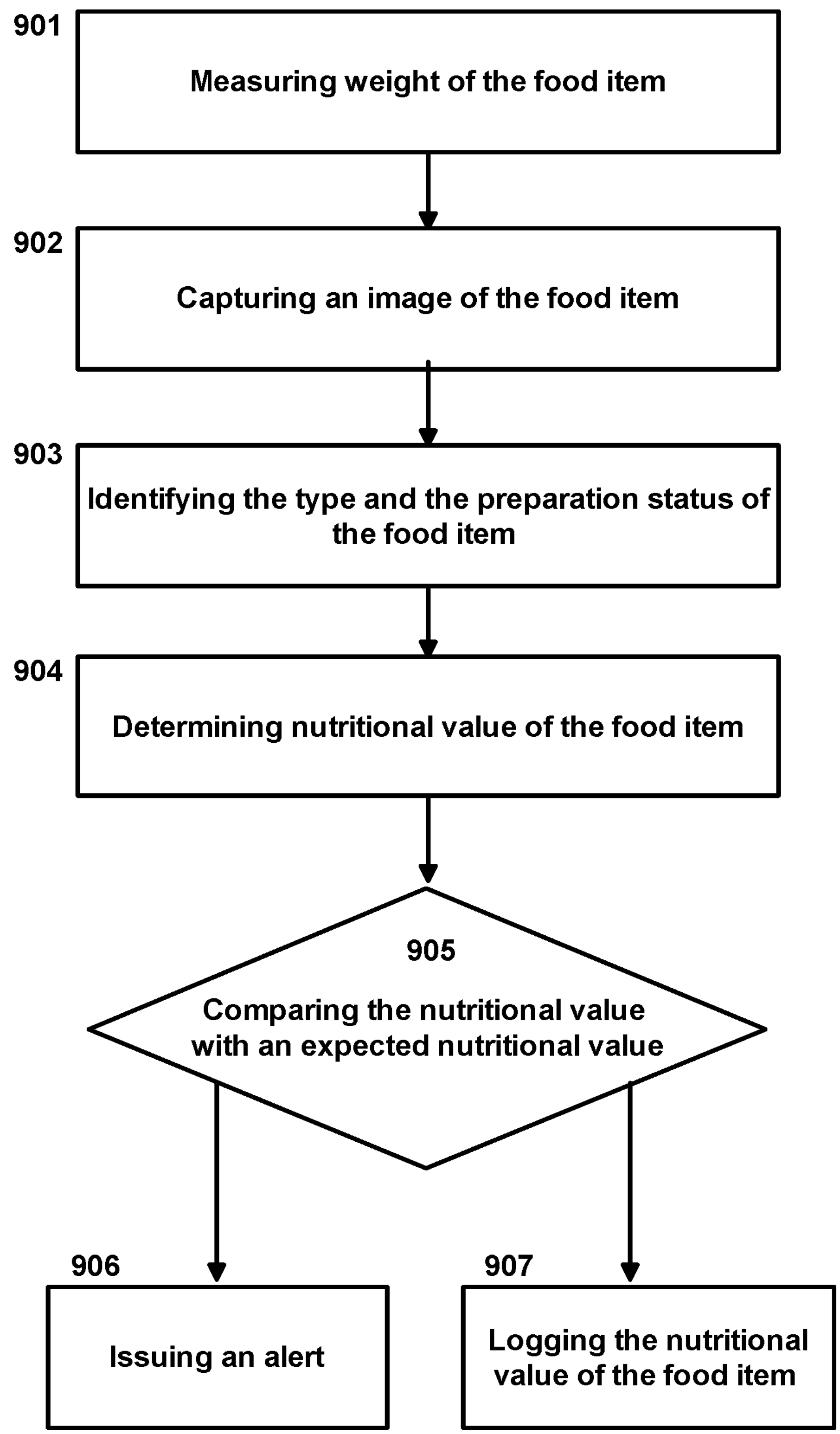
FIG. 9 provides a flowchart describing an exemplary method for issuing an alert.

FIG. 9 provides a flowchart describing an exemplary method for issuing an alert. The method described may be provided by the one or more processors. In step 901, the weight of the food item is measured. Next, the image of the food item is captured 902 to identify the type of the food item and the preparation status of the food item 903. The nutritional value of the food item may be determined 904 based on the weight, the type, and the preparations status of the food item. The nutritional value determined by the one or more processors may then be compared with an expected nutritional value 905. If the nutritional value exceeds the expected nutritional value, the alert may be issued 906. Alternatively, if the nutritional value is on par or below the expected nutritional value, the nutritional value may be logged in the storage unit and added to the user's eating behavior or pattern.

Figure 10:
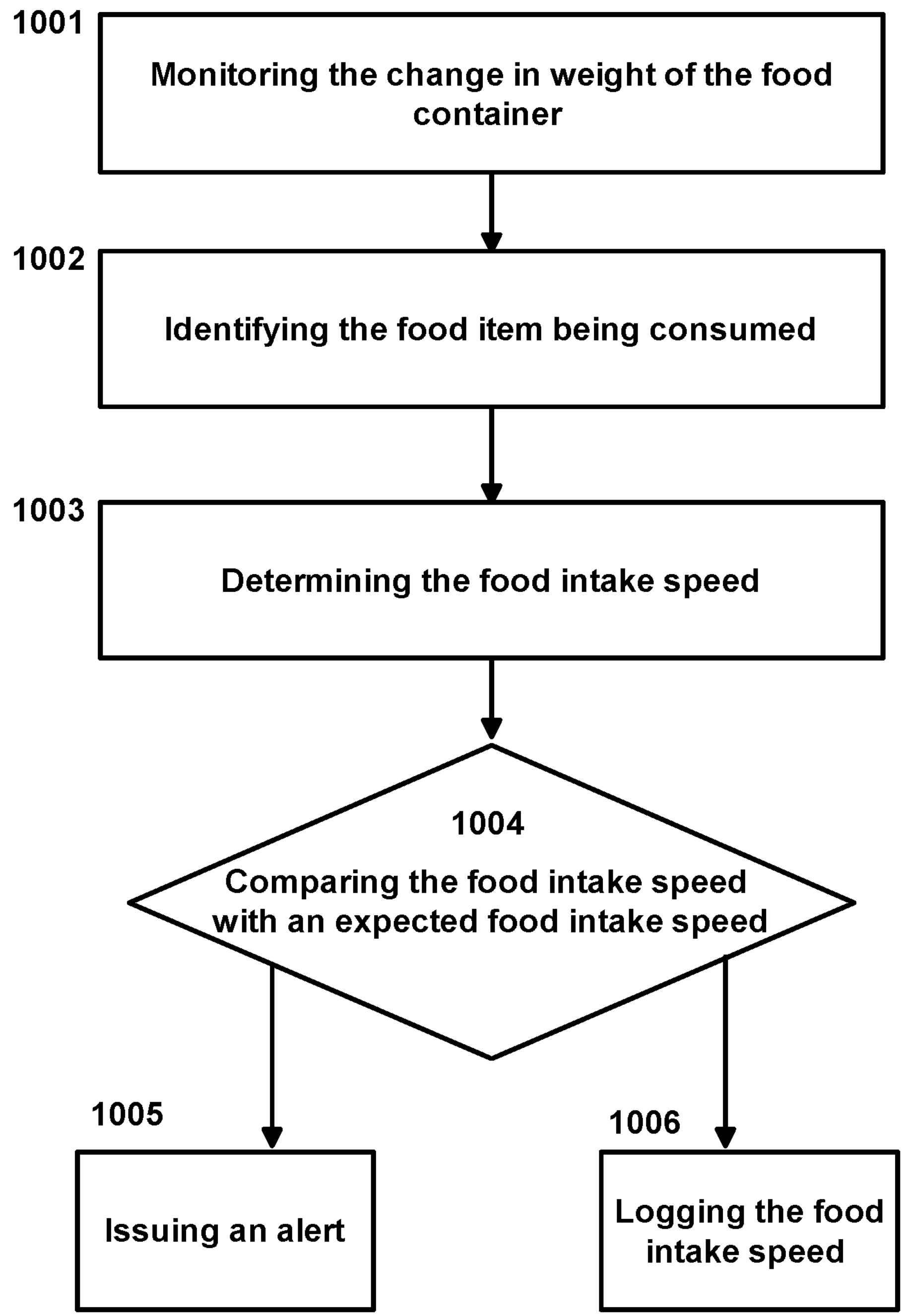
FIG. 10 provides a flowchart describing another exemplary method for issuing an alert.

FIG. 10 provides a flowchart describing another exemplary method for issuing an alert. The weight of the food container may be monitored 1001 by the one or more processors as the user consumes the food item. With the food identification sensor, the type and the preparation status of food item being consumed by the user may be identified 1002. As the weight of the food reduces, the food intake speed may be determined by the one or more processors 1003. The food intake speed may then be compared with an expected food intake speed 1004 stored in the storage unit. In the instances where the food intake speed exceeds the expected food intake speed, an alert may be issued 1005. Otherwise, the food intake speed may be recorded 1006 to analyze the user's eating behavior and pattern over time.

While several variations of the present invention have been illustrated by way of example in preferred or particular embodiments, it is apparent that further embodiments could be developed within the spirit and scope of the present 10 invention, or the inventive concept thereof. However, it is to be expressly understood that such modifications and adaptations are within the spirit and scope of the present invention, and are inclusive, but not limited to the following appended claims as set forth.

Those skilled in the art will readily observe that numerous modifications, applications and alterations of the device and method may be made while retaining the teachings of the present invention.

What is claimed is:

1. A system for monitoring a food item being consumed by a user, comprising:

a food container forming one or more partitions to receive and retain the food item;

a weight sensor placed within the food container, positioned to measure a weight of the food item being received by the one or more partitions;

one or more cameras, each of the one or more cameras being respectively positioned to identify a type and a preparation status of the food item, each of the one or more cameras capturing an image of the food item, the image comprising at least a portion of the food item; and wherein the weight sensor and the one or more cameras are in communication with one or more processors, the one or more processors being configured to determine a nutritional value of the food item based on the type, the preparation status, and the weight, the type and the preparation status being identified by comparing properties of the food item identified from the captured image to reference properties corresponding to one of a various types of food item stored in a storage unit, the preparation status indicating a preparation method of the food item, the one or more processors in communication with the storage unit.

2. The system of claim 1 wherein the preparation status includes an additional cooking ingredient, the additional cooking ingredient, added when preparing the food item, being identified based on the preparation method.

3. The system of claim 1 wherein the food item is a mixture of a plurality of ingredients, the type being identified by individually identifying each of the plurality of ingredients, each of the plurality of ingredients being identified by comparing properties of each of the plurality of ingredients from the captured image to reference properties corresponding to one of a various ingredients stored in the storage unit.

4. The system of claim 1 wherein the one or more processors controls the one or more cameras, positioning the one or more cameras to at least one of a desired angle and a desired proximity, with regards to the food item.

5. The system of claim 1 wherein the one or more processors is configured to:

compare the nutritional value to an expected nutritional value, the expected nutritional value being stored by the storage unit; and issue an alert, the alert being presented by the computerized user interface, the alert being issued when the nutritional value is at least one of:

more the expected nutritional value;

equal to the expected nutritional value; and less than the expected nutritional value.

6. The system of claim 1 wherein the one or more processors is configured to:

identify a food intake speed, the food intake speed representing the speed in which the user consumes the food item placed in the one or more partitions, based on at least one of:

change in the weight of the food item as they are consumed by the user, the weight being monitored with the weight sensor; and a motion monitoring unit observing the movement of the user as the user consumes the food item, the motion monitoring unit being in communication with the one or more processors;

compare the food intake speed to an expected food intake speed, the expected food intake speed being stored by the storage unit; and issue an alert, the alert being presented by the computerized user interface, the alert being issued when the food intake speed is at least one of:

more the expected food intake speed;

equal to the expected food intake speed; and less than the expected food intake speed.

7. The system of claim 1 further comprising a surface sensor, the surface sensor identifying a food composition of the food item, the type and the preparation status of the food item being identified by comparing the food composition identified by the surface sensor to the reference properties, the properties comprising food compositions of the various types of food item, the surface sensor being positioned to identify the food composition.

8. The system of claim 1 wherein the one or more cameras is equipped with a spectrometer, the spectrometer detecting the properties of the food item, the properties comprising one or more of, food composition, chemical composition, pesticide, allergen, and pathogen, wherein the spectrometer is in communication with the one or more processors.

9. The system of claim 8 wherein the spectrometer is at least one of a hyperspectral imaging spectrometer and a multispectral imaging spectrometer.

10. The system of claim 1 wherein the one or more cameras is a depth-sensing camera that can identify a depth of the food item.

11. The system of claim 10 wherein the one or more processors is configured to:

identify a depth profile of the food item; and determine a volume of the food item.

12. The system of claim 1 wherein the one or more processors is configured to estimate a volume of the food item by identifying a surface area of the food item in the image, the surface area being identified based on the number of pixels the food item occupies within the image.

13. The system of claim 1 wherein the one or more processors is configured to determine a volume of the food item, the volume being determined based on two or more images of the food item, captured by the one or more cameras at multiple views.

14. The system of claim 1 wherein the one or more processors is configured to determine a volume of the food item, the volume being determined by identifying a density of the food item from a type-to-density list stored in the storage unit and the weight of the food item.

15. The system of claim 1 wherein the one or more processors is configured to:

identify a food intake frequency, the food intake frequency representing the frequency in which the user consumes the food item placed in the one or more partitions, based on at least one of:

change in the weight of the food item as they are consumed by the user, the weight being monitored with the weight sensor; and a motion monitoring unit observing the movement of the user as the user consumes the food item, the motion monitoring unit being in communication with the one or more processors; and identify a pattern in the food intake frequency over time.

16. The system of claim 1 wherein the one or more processors is configured to:

identify a food intake amount, the food intake amount representing the amount of the food item the user consumes at each intake, by monitoring the change in the weight of the food item as they are consumed by the user; and identify a pattern in the food intake amount over time.

17. A method for monitoring a food item being consumed by a user, the food item being received and retained by a food container, the food container comprising one or more partitions formed by the food container to receive and retain the food item, the method comprising the steps of:

receiving, by a one or more processors, a weight of the food item from a weight sensor, the weight sensor being placed within the food container;

identifying a type and a preparation status of the food item, by the one or more processors, based on an image captured by one or more cameras, the image comprising at least a portion of the food item, each of the one or more cameras being respectively positioned to identify the type and the preparation status of the food item, the one or more cameras being in communication with the one or more processors, the one or more processors being further in communication with a storage unit, wherein the type and the preparation status are identified by comparing properties of the food item identified from the captured image to reference properties corresponding to one of a various types of food item stored in the storage unit, the preparation status indicating a preparation method of the food item; and determining, by the one or more processors, a nutritional value of the food item based on the weight, the preparation status, and the type of the food item.

18. The method of claim 17 wherein the preparation status includes an additional cooking ingredient, the additional cooking ingredient, added when preparing the food item, being identified by the one or more processors based on the preparation method.

19. The method of claim 17 wherein the food item is a mixture of a plurality of ingredients, the type being identified by individually identifying each of the plurality of ingredients, with the one or more processors, each of the plurality of ingredients being identified by comparing properties of each of the plurality of ingredients from the captured image to reference properties corresponding to one of a various ingredients stored in the storage unit.

20. The method of claim 17 further comprising the steps of:

comparing, by the one or more processors, the nutritional value to an expected nutritional value, the expected nutritional value being stored by the storage unit; and issuing an alert, by the one or more processors, the alert being presented by a computerized user interface in communication with the one or more processors, the alert being issued when the nutritional value is at least one of:

more the expected nutritional value;

equal to the expected nutritional value; and less than the expected nutritional value.

21. The method of claim 17 further comprising the steps of:

identifying, by the one or more processors, a food intake speed, the food intake speed representing the speed in which the user consumes the food item placed in the one or more partitions, based on at least one of:

change in the weight of the food item as they are consumed by the user; and movement of the user as the user consumes the food item, the movement being monitored by a motion monitoring unit, the motion monitoring unit being in communication with the one or more processors;

comparing, by the one or more processors, the food intake speed to an expected food intake speed, the expected food intake speed being stored by the storage unit; and issuing an alert, by the one or more processors, the alert being presented by a computerized user interface in communication with the one or more processors, the alert being issued when the food intake speed is at least one of:

more the expected food intake speed;

equal to the expected food intake speed; and less than the expected food intake speed.

22. The method of claim 17 further comprising the step of identifying, by a surface sensor, a food composition of the food item, the type and the preparation status of the food item being identified by comparing the food composition identified by the surface sensor to the reference properties, the properties comprising food compositions of the various types of food item, the surface sensor being in communication with the one or more processors, the surface sensor being positioned to identify the food composition.

23. The method of claim 17 further comprising the step of providing, by the one or more processors, a recommended meal plan based on at least one of:

the nutritional value being consumed by the user over time; and an input from the user received by a computerized user interface, the computerized user interface being in communication with the one or more processors.

24. The method of claim 17 further comprising the step of detecting, with the one or more cameras equipped with a spectrometer, the properties of the food item, the properties comprising one or more of, food composition, chemical composition, pesticide, allergen, and pathogen, wherein the spectrometer is in communication with the one or more processors.

25. The method of claim 24 wherein the spectrometer is at least one of a hyperspectral imaging spectrometer and a multispectral imaging spectrometer.

26. The method of claim 17 wherein the one or more cameras is a depth-sensing camera that can identify a depth of the food item, the method further comprising the steps of:

identifying, with the one or more processors, a depth profile of the food item; and determining, with the one or more processors, a volume of the food item.

27. The method of claim 17 further comprising the step of estimating, with the one or more processors, a volume of the food item by identifying a surface area of the food item in the image, the surface area being identified based on the number of pixels the food item occupies within the image.

28. The method of claim 17 further comprising the step of determining, with the one or more processors, a volume of the food item based on two or more images of the food item, captured by the one or more cameras at multiple views.

29. The method of claim 17 further comprising the step of determining, with the one or more processors, a volume of the food item by identifying a density of the food item from a type-to-density list stored in the storage unit and the weight of the food item.

30. The method of claim 17 further comprising the steps of:

identifying, by the one or more processors, a food intake frequency, the food intake frequency representing the frequency in which the user consumes the food item placed in the one or more partitions, based on at least one of:

change in the weight of the food item as they are consumed by the user, the weight being monitored with the weight sensor; and a motion monitoring unit observing the movement of the user as the user consumes the food item, the motion monitoring unit being in communication with the one or more processors; and identifying, by the one or more processors, a pattern in the food intake frequency over time.

31. The method of claim 17 further comprising the steps of:

identifying a food intake amount, by the one or more processors, the food intake amount representing the amount of the food item the user consumes at each intake, by monitoring the change in the weight of the food item as they are consumed by the user; and identifying, by the one or more processors, a pattern in the food intake amount over time.

32. A system for monitoring a food item being consumed by a user, comprising:

a food container forming one or more partitions to receive and retain the food item;

a weight sensor placed within the food container, positioned to measure a weight of the food item being received by the one or more partitions;

a spectrometer positioned to identify a type and a preparation status of the food item, the spectrometer detecting properties of the food item, the properties comprising chemical composition of the food item; and wherein the weight sensor and the spectrometer are in communication with one or more processors, the one or more processors being configured to determine a nutritional value of the food item based on the type, the preparation status, and the weight, the type and the preparation status being identified by comparing the detected properties of the food item to reference properties corresponding to one of a various types of food item stored in a storage unit, the preparation status indicating a preparation method of the food item, the one or more processors in communication with the storage unit.

* * * * *